United States Patent [19]

Bauer

[11] 3,947,971

[45] Apr. 6, 1976

[54] FABRIC SOFTENER AND DISPENSER

[75] Inventor: Henry Bauer, Miraleste, Calif.

[73] Assignee: John Levey, Westlake Village, Calif.

[22] Filed: Nov. 6, 1974

[21] Appl. No.: 521,361

[52] U.S. Cl. ........................ 34/60; 239/60; 134/93; 15/244 C

[51] Int. Cl.² ...................... F26B 19/00; A61L 9/04

[58] Field of Search ............ 239/60; 134/93; 34/60; 206/0.5, 0.82; 15/104.93, 104.94, 244 C

[56] References Cited

UNITED STATES PATENTS

| | | | |
|---|---|---|---|
| 1,577,861 | 3/1926 | Henry | 15/244 C |
| 1,748,406 | 2/1930 | Blair | 15/244 C |
| 1,909,966 | 5/1933 | Jones | 15/244 C |
| 1,912,224 | 5/1933 | Schimel | 15/244 C |
| 2,204,202 | 6/1940 | Zimmerman | 15/244 C |
| 2,204,203 | 6/1940 | Zimmerman | 15/244 C |
| 2,687,729 | 8/1954 | Slavin | 15/244 C |
| 3,570,036 | 3/1971 | Gilchrist et al. | 15/104.94 |
| 3,633,538 | 1/1972 | Hoeflin | 34/60 UX |
| 3,698,095 | 10/1972 | Grand et al. | 34/60 X |
| 3,836,077 | 9/1974 | Skildum | 239/60 |
| 3,870,145 | 3/1975 | Mizuno | 34/60 X |
| R21,399 | 3/1940 | Zimmerman | 15/244 C |

*Primary Examiner*—Robert S. Ward, Jr.
*Attorney, Agent, or Firm*—William H. Pavitt, Jr.

[57] ABSTRACT

A combination including a packet having a space therein containing a tablet formed of a solid fabric softener composition which is partially water soluble. The packet is formed from a pair of flexible porous open-celled sheets which are joined together in face-to-face relation. A flexible opening formed in the packet leads to the space defined between the pair of flexible porous open-celled sheets. The opening has a normally closed position when the sheets which form the packet are in their expanded condition. However, the opening is expandable to an open position by squeezing the sides of the packet in a direction along the axis of the opening.

The sheets forming the packet have a thickness that is sufficient to reduce flow of water through the sheets to a level which prevents complete solution of the tablet during a single use while, however, permitting partial solution of the tablet with migration of dissolved fabric softener composition from the interior to the exterior of the packet. In usage, the combination of the packet and tablet is placed in a dryer which contains a damp fabric load and the fabric softener composition migrates through the walls of the flexible open-celled sheets by a kneading action. The kneading action first involves the absorption of water by the packet from the load with the water passing through the flexible porous open-celled sheets to solubilize fabric softener composition on the exterior of the tablet. The solubilized fabric softener composition then passes outwardly through the walls of the open-celled sheets into contact with the fabric load as the packet is compressed by the weight of the fabric load during tumbling of the load within a dryer.

10 Claims, 4 Drawing Figures

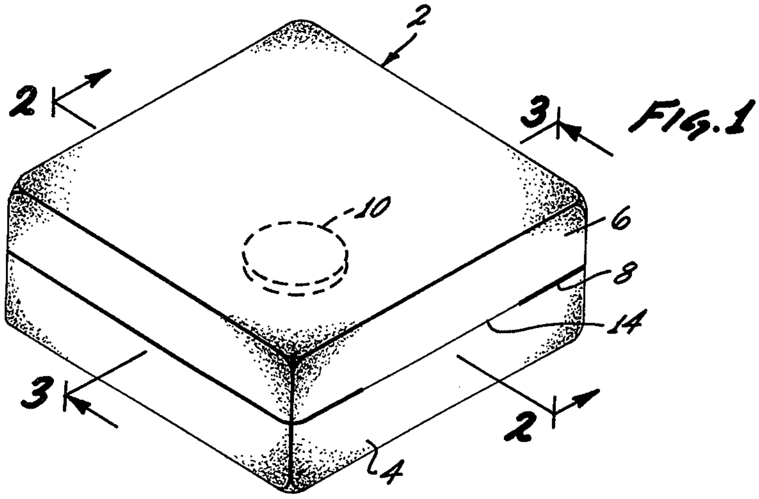
FIG. 1
FIG. 2
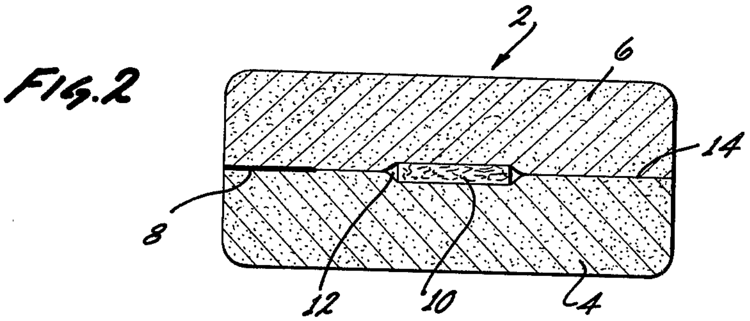
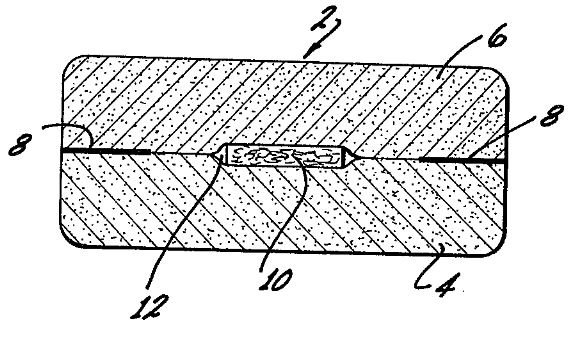
FIG. 3
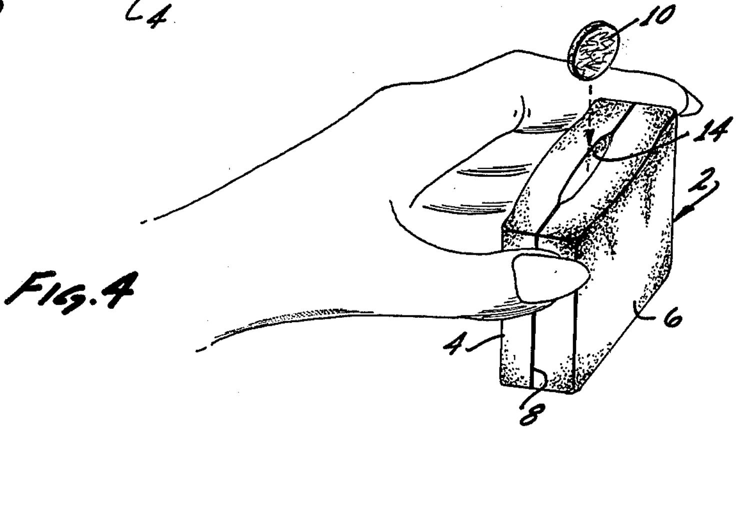
FIG. 4

FABRIC SOFTENER AND DISPENSER

The use of fabric softening compositions is known to provide softness to textile fabrics. Also, it is known that many fabric softeners act to reduce static electricity in a treated fabric which reduces the adherence of lint or dust to the fabric. By treatment of a fabric with a fabric softener, the fabric is, thus, more comfortable to wear, easier to iron, and has fewer wrinkles.

As used presently, a fabric softener is generally added in a liquid form to a load of washing. For example, the fabric softener may be present in the added liquid as a 10 percent solution of fabric softener and one cup of the liquid may be added to each load of washing. This method of adding a fabric softener to a load of laundry is generally unsatisfactory since the bulk of the fabric softener is wasted. The fabric softener is diluted by the rinse water and the diluted fabric softener is then discharged from the washing machine to the drain.

As a solution to the above problem, it has been previously proposed to treat fabrics with a fabric softener by coating or impregnating a porous carrier fabric with the fabric softener and then adding a swatch of the carrier fabric to a clothes dryer. During drying of the fabric load, the fabric softener is liquified by the heat of the dryer and is brought into contact with the fabric load. In regard to this method of contacting a fabric load with a fabric softener, reference is made to U.S. Pat. Nos. 3,632,396; 3,686,025, and 3,743,534.

When a fabric softener is coated or impregnated onto a carrier fabric, the quantity of fabric softener which is present on the carrier fabric is generally limited to a relatively small quantity. Thus, the impregnated or coated carrier fabric is generally usable for only one application of the softener. On placement of a swatch of carrier fabric within a clothes dryer, the swatch of coated or impregnated carrier fabric is added to the load of fabric within the dryer and the fabric softener is transferred from the carrier fabric to the load of fabric during the drying operation. On completion of the drying operation, the swatch of carrier fabric is depleted of fabric softener and a new swatch of the carrier fabric is then used for the next load, etc.

The transfer mechanism which has been utilized for treatment of a fabric load with a fabric softener within a dryer has generally involved melting of the fabric softener by heating it to a temperature in excess of its melting or softening point. In general, this method of applying the fabric softener to the load is not desirable since it may produce a non-uniform application of the softener to the fabric load. For example, on melting of the fabric softener, the relatively small quantity of fabric softener on the swatch of carrier fabric may be transferred to only a portion of the fabric load. Then, depending on the duration of the drying cycle and the quantity of fabrics in the fabric load, the fabric softener may not be evenly distributed among the fabric load and some fabrics may receive a heavier treatment of fabric softener while other fabrics in the load receive a lighter treatment of fabric softener.

In accord with the present invention, a fabric softener is added to a fabric load within a dryer by addition of a fabric softener combination to the dryer, which includes a packet enclosing a tablet of a solid fabric softener composition. The packet is formed from a pair of flexible porous open-celled sheets which are joined together in face-to-face relation. A flexible opening is formed in the packet with the opening having a normally closed position when the flexible sheets are in their expanded condition. However, the opening is expandable to an open position by squeezing the sides of the packet in a direction along the axis of the opening. With the flexible opening expanded to its open position, the tablet may be inserted through the opening and into a space defined between the flexible porous open-celled sheets.

The flexible porous open-celled sheets which make up the packet have a thickness, which is generally in the order of ½ inches or more, that is sufficient to reduce the flow of water from a wet fabric load through the porous sheets to a level which prevents the complete solution of the tablet by the water in the load. However, at the same time, the porous open-celled structure of the flexible sheets permits a sufficient flow of water through the sheets to partially dissolve the tablet by solubilizing fabric softener composition on the exterior surface of the tablet. The solubilized fabric softener composition is then permitted to migrate from the interior to the exterior of the packet with the result that the solubilized fabric softener composition is brought into contact with the fabric load within the dryer.

The flexible or resilient nature of the porous open-celled sheets which form the packet permit release of the fabric softener composition from the packet through a kneading action as the packet is tumbled within a dryer in contact with a wet fabric load. The tumbling of the wet fabric load within the dryer in contact with the flexible packet subjects the packet to a kneading action which promotes a slow and controlled release of the fabric softener composition from the packet into the fabric load. During rotation of the dryer drum to position the flexible packet adjacent the top of the drum, water will pass from the wet fabric load through the flexible porous open-celled sheets of the packet into contact with the exterior surface of the tablet of fabric softener. This produces solubilization of the fabric softener composition on the exterior of the tablet. Then, on continued rotation of the dryer drum to position the flexible packet at the bottom of the drum, the weight of the wet fabric load compresses the flexible porous open-celled sheets to squeeze the solubilized fabric softener composition from the packet. The solubilized fabric softener composition, thus, passes through the walls of the open-celled sheets into contact with the fabric load as the packet is kneaded or squeezed by the weight of the wet fabric load.

During each revolution of the dryer drum, the flexible packet is alternately squeezed and then permitted to expand with the packet releasing solubilized fabric softener composition to the load during squeezing and absorbing water from the load during expansion. This kneading action of the flexible packet by the weight of the wet fabric load during rotation of the dryer drum provides a slow and controlled release of the solubilized fabric softener composition from the packet into contact with the fabric load within the dryer. This, then, provides a more uniform treatment of the fabric load with the fabric softener composition due to the slow and controlled release of the fabric softener composition from the flexible packet. Also, because of the slow and controlled release rate of the fabric softener composition from the flexible packet, the flexible packet and tablet of fabric softener composition may be used to treat a number of fabric loads with the fabric softener composition.

In the testing of the combination of the present invention, I have found that a single tablet of fabric softener composition may be used to treat as many as ten loads of fabric with the fabric softener before replacement of the tablet becomes necessary. The number of fabric loads which may be treated with a single tablet of fabric softener composition will, of course, vary depending upon the size of the tablet of fabric softener composition that is used. Also, the size of the loads being treated, their degree of wetness, etc., are factors which will determine, to some extent, the number of fabric loads that may be treated with a single tablet.

Due to the flexible nature of the sheets which form the packet, the sheets may be compressed by the user to feel the size of the tablet and determine the rate at which the fabric softener is being used. When compressing of the flexible sheets in this manner indicates that the tablet of solid fabric softener has been almost completely used up, a new tablet may then be added to the packet by simply expanding the packet opening to its open position and inserting a new tablet into the space between the pair of flexible porous open-celled sheets.

To further illustrate the invention, reference is made to the enclosed drawing in which:

FIG. 1 is a perspective view of a packet formed from a pair of flexible porous open-celled sheets joined together in face-to-face relation to define a space between the sheets which encloses a tablet of a solid fabric softener composition;

FIG. 2 is a sectional view taken along the line 2—2 of FIG. 1 to illustrate the position of the tablet within the space formed between the flexible porous open-celled sheets with the sheets being left unsealed along a portion of one edge to provide a flexible opening from the exterior of the packet into the space containing the fabric softener tablet;

FIG. 3 is a sectional view taken along the line 3—3 of FIG. 1 to illustrate the connection of the flexible porous open-celled sheets along opposite edges of the sheets in forming the space between the flexible sheets which contains the fabric softener tablet, and FIG. 4 is a perspective view illustrating the manner in which the flexible opening into the packet may be expanded to an open position by squeezing of the packet along opposite sides in a direction along the axis of the opening.

Turning to FIG. 1, a flexible packet 2 is formed by the joining of a bottom sheet 4 and a top sheet 6. Each of the sheets 4 and 6 is a flexible porous open-celled material such as a flexible polyurethane foam. The porous open-celled nature of the sheets 4 and 6 and permits the flow of water through the sheets when the packet 2 is in contact with a wet fabric load within a dryer.

The flexible porous open-celled sheets 4 and 6 are sealed together about their edges along a seal line 8 and a tablet 10 formed of a solid fabric softener composition is retained in the space formed between the sheets. On the flow of water through the walls of sheets 4 and 6, as will be described, the water contacts the exterior surface of the tablet 10. This causes solubilization of the fabric softener composition on the exterior of the tablet 10 with the solubilized fabric softener composition then passing through the walls of the open-celled sheets 4 and 6 into contact with the wet fabric load.

Turning to FIG. 2, which is a cross-sectional view taken along line 2—2 of FIG. 1, a space 12 is formed between the bottom sheet 4 and top sheet 6 which contains the tablet 10 of fabric softener. As indicated, the space 12 may be formed simply by inserting the tablet 10 between the sheets 4 and 6 to displace the flexible material in accommodating the volume of the tablet. Also, if desired, the space 12 may be formed by the removal of material from the inner surfaces of the sheets 4 and 6 to form a cavity having the same size as the tablet 10 with the sheets being reduced in thickness in the areas of the sheets positioned above the cavity.

As illustrated in FIG. 2, an opening 14 is formed along unsealed edges of the sheets 4 and 6 with the opening leading to the space 12. The opening 14, as shown, is normally closed due to the resiliency of the porous open-celled material forming the sheets 4 and 6. Due to the resiliency of the sheets 4 and 6, the sheets act, in the manner of a spring, to expand to their full size which maintains the opening 14 in its closed position shown in FIG. 2.

Turning to FIG. 3, which is a sectional view taken along line 3—3 of FIG. 1, the sheets 4 and 6 are sealed together about their edges along a seal line 8 to completely enclose the tablet 10 except at the flexible opening 14. The thickness of the tablet 10 will decrease during usage of the tablet and flexible packet 2 with water moving from a wet fabric load through the walls of the sheets 4 and 6 to solubilize the fabric softener composition on the surface of the tablet. As the tablet 10 becomes depleted with repeated use of the flexible packet 2, the user may readily check the condition of the tablet simply by compressing the packet in the areas above the tablet. When compressing of the packet 2 indicates that the tablet 10 is almost depleted, a new tablet may be added by expanding the opening 14 to its open position and inserting a new tablet into the space 12 between sheets 4 and 6.

As illustrated in FIG. 4, the opening 14 may be expanded to its open position simply by grasping the sides of the flexible packet 2 and compressing the packet in a direction along the axis of the opening 14. With the opening 14 being, thus, expanded to its open position, a new tablet 10 may be inserted into the space 12 through the opening.

The fabric softener composition, as described, may be any solid fabric softener which is moderately soluble in water. In the formation of the tablet 10, the solid fabric softener composition may be converted to a tablet by placing the powdered fabric softener composition into a mold and then compressing the powdered material within the mold through use of a standard pelleting press. If desired, the fabric softener composition may also include minor amounts of conventional additives such as a perfume or a minor amount of a conventional binder material such as starch to assist in the formation of the tablet. Additionally, a material such as pyrogenic silica may be added to the fabric softener composition to impart the properties to the composition which may be desired in forming a fabric softener tablet.

Preferably, the fabric softener composition is a cationic quaternary ammonium salt and may also be a quaternary imidazolinium salt. Typically, a quaternary ammonium salt may be employed as the fabric softener in which four organic groups are bonded to a nitrogen atom having a charge of +1 which is combined with an anion having a charge of −1. The anion may, for example, be a halide and specifically may be a chloride ion. The anion in the quaternary ammonium salt may also, for example, be an acetate, phosphate, nitrate, or a methyl sulfate radical. The organic groups which are bonded to the charged nitrogen atom in the cationic quaternary ammonium salt may be a benzyl group or, for example, an alkyl group containing from 1 to about 20 carbon atoms. Preferably, at least one of the organic groups that is bonded to the nitrogen atom is an alkyl group containing from about 12 to about 20 carbon atoms with the alkyl group being straight or branched chained and being either saturated or unsaturated.

Among the cationic quaternary ammonium salts which are most widely used as softening agents are dialkyl dimethyl ammonium chloride or alkyl trimethyl ammonium chloride in which the alkyl group or groups each contain from about 12 to 20 carbon atoms and are derived from a long chain fatty acid such as hydrogenated tallow. Long chain fatty acid alkyl groups referred to by the term "tallow" refer to alkyl groups which contain from 16 to 18 carbon atoms while the term "tallowalkoxy" refers to an alkyl ether radical in which the alkyl group contains from 16 to 18 carbon atoms.

As examples of suitable cationic quaternary ammonium salts which may be utilized as the fabric softening composition in the tablet 10, there are the compounds tallow trimethyl ammonium chloride, tallow dimethyl (3-tallowalkoxypropyl) ammonium chloride, ditallow dimethyl ammonium chloride, ditallow dimethyl ammonium methyl sulfate, eicosyltrimethyl ammonium chloride, and dieicosyldimethyl ammonium chloride.

Still further examples of suitable cationic softening agents are the compounds dodecyltrimethyl ammonium chloride, didodecyldimethyl ammonium chloride, tetradecyltrimethyl ammonium chloride, ditetradecyldimethyl ammonium chloride, pentadecyltrimethyl ammonium chloride, dipentadecyldimethyl ammonium chloride, didodecyldiethyl ammonium chloride, didodecyldipropyl ammonium chloride, ditallowdipropyl ammonium chloride, tallowtrimethyl ammonium acetate, tallowdimethyl benzyl ammonium nitrate, ditallowdipropyl ammonium phosphate, and the like.

In general, the fabric softener compositions employed in the tablet 10 will have a melting point of about 120° to about 190° F. and preferably about 150° F. or higher. A clothes dryer may operate at temperatures ranging from about 75° F. when the wet load is first placed in the dryer up to as high as about 170° F. during the latter portions of the drying cycle. It is not desired that the fabric softener composition in the tablet 10 should be completely melt at the temperatures encountered within the clothes dryer. However, if the tablet 10 does melt, its melting point is sufficiently high that the melted material is quite viscous and will not flow through the porous sheets 4 and 6 but is retained within the packet 2. The transfer of fabric softener composition from the tablet 10 to the wet load, thus, occurs through solubilization of the fabric softener composition on the surface of the tablet 10 with the solution of fabric softener composition then passing outwardly through the walls of the sheets 4 and 6 into contact with the wet fabric load.

The nature of the porous, open-celled sheets 4 and 6 also serves to protect the tablet 10 from relatively high temperatures which may be encountered within a clothes dryer. The porous sheets 4 and 6 take up water from the wet fabric load, as described, during the initial phases of the drying cycle and a solution of the fabric softener composition is then released through the walls of the sheets to the fabric load as the packet 2 is kneaded by the weight of the wet fabric load during rotation of the dryer drum. The kneading of the flexible packet 2 by the weight of the wet fabric load in contact therewith provides a slow and controlled release of fabric softener composition from the tablet 10 through the walls of the flexible porous, open-celled sheets 4 and 6. The water which is absorbed by the porous, open-celled sheets 4 and 6 from the wet fabric load, in addition to providing controlled slow migration of fabric softener composition from the tablet 10 into the wet fabric load, also serves to maintain the temperature within the space 12 at a level which protects the fabric softener composition tablet 10 from the affects of excessive temperatures within the clothes dryer.

As described, it is important in the functioning of the flexible packet 2 and the tablet 10 of fabric softener composition that the fabric softener composition be released through the walls of the porous open-celled sheets 4 and 6 at a slow and controlled rate. Accordingly, the thickness of the walls of the sheets 4 and 6 is of considerable importance in the functioning of the packet 2 to cause a slow and controlled release of fabric softener composition to the wet fabric load. The thickness of the walls of sheets 4 and 6, which may vary depending upon the particular nature of the porous material forming the sheets, is sufficient to reduce the flow of water through the walls to a level which prevents complete solution of the tablet 10 during contact with a wet fabric load since this would cause release of the fabric softener composition at too high a rate with the tablet of fabric softener composition being depleted during a single use application. While maintaining the flow rate of water through the walls of the sheets 4 and 6 at a sufficiently low level to prevent complete solution of the tablet 10, the walls of the sheets do, however, permit water flow through the walls at a rate sufficient to solubilize the fabric softener composition on the exterior surface of tablet 10. The solubilized fabric softener composition is then released slowly from the flexible packet 2 as the packet is successively squeezed or kneaded by the wet fabric load during rotation of the dryer drum.

Preferably, the flexible porous open-celled sheets 4 and 6 are formed of a foamed, flexible, porous, open-celled polyurethane. Such materials are well known and are widely used in commerce, for example, as packaging materials. Thus, a detailed description of a foamed polyurethane will not be provided.

Suffice it to say, however, that a foamed, flexible polyurethane, as may be employed in the present invention, has a plurality of very fine pore openings and an open-celled structure. This combination of fine pore openings, together with a porous open-celled structure, provides a slow and controlled migration of fabric softener composition through the walls of the flexible sheets 4 and 6 as the packet 2 is kneaded within a dryer by the weight of the wet fabric load as the load is tumbled. In using a foamed, flexible, porous, open-celled polyurethane material for formation of the sheets 4 and 6, the sheets will preferably have a thickness of about ½ inches or more, e.g., about ½ inch to about 1½ inches. This thickness of material provides the desired slow controlled release of the fabric softener composition through the walls of the sheets 4 and 6 as the packet 2 is kneaded by the wet fabric load within a clothes dryer.

While the thickness of the sheets 4 and 6 will determine the release rate of fabric softener composition from the tablet 10, the size of the tablet is also a factor in the rate of release of the fabric softener composition. As the size of the tablet 10 is increased, the exterior surface area of the tablet is also increased which increases the rate of release of fabric softener composition to the wet fabric load. While the size of tablet 10 may be varied, I have found that a relatively small tablet weighing, for example, about one ounce, is quite suitable for treating a number of fabric loads with a fabric softener within a conventional clothes dryer. Typically, the amount of fabric softener composition which is transferred from the surface of the tablet 10 to the wet fabric load during a single drying cycle may be in the order of about 0.1 to about 0.2 ounces. Thus, when the weight of the tablet 10 is about one ounce, the tablet will have a use life of about 5 to about 10 loads of fabrics.

In tests which were performed, a tablet weighing one ounce was made up from di-stearyl dimethyl ammonium chloride (Arquad 2 HT-75 provided by the AR MAK Company of Chicago, Illinois). This fabric softener, which is supplied at a 75 percent concentration in admixture with isopropyl alcohol, was admixed with 2 percent by weight of a standard lemon perfume and the mixture was then compounded into tablets in a conventional pelleting press. The tablets, which each weighed approximately one ounce, were then inserted into a flexible packet 2, as described, in which the sheets 4 and 6 of the packet measured 3 inches by 6 inches and each sheet was approximately 1 inch thick. The sheets 4 and 6 which were employed were made from a fine pore, flexible, foamed, porous, open-celled polyether urethane.

During testing of the combination of the flexible packet 2 and the tablet 10 of fabric softening composition, the packet combination was simply added to a conventional clothes dryer having a rotating dryer drum. The flexible packet 2 was then tumbled within the drum in contact with the wet fabric load to produce kneading of the flexible packet, as described, in providing a slow and controlled release of fabric softener composition from the tablet 10 through the walls of the flexible packet. In these tests, it was found that the first three minutes of the drying cycle were of greatest importance in the transfer of fabric softener composition to the fabric load since the load was then wet and water was transferred through the walls of the flexible, porous, open-celled sheets 4 and 6 to provide solution of the fabric softener composition from the surface of tablet 10 with the solubilized fabric softener composition being transferred at a slow controlled rate through the walls of the sheets. After the first three minutes of the drying cycle, the transfer rate of fabric softener composition through the walls of the flexible packet 2 was found to decrease sharply. By this time, the fabric load was not in a fully wetted state to provide the maximum availability of water, and maximum kneading of the flexible packet 2 which provide maximum transfer of the fabric softener composition through the walls of the flexible packet to the fabric load.

Preferably, the porous, open-celled sheets 4 and 6 have a fine pore structure. By a fine pore structure, I refer to pore openings which range from about one-ninety-sixth to about one-thirty-second of an inch.

As described, the flexible packet and fabric softener tablet combination of the invention is used by adding the packet to a wet fabric load which is then tumbled within a conventional clothes dryer. In the operation of the dryer, the temperature may increase to as high as 170° F. Thus, the flexible, porous, open-celled material forming the flexible packet 2 must be resistant to high temperatures such that it will not be adversely affected by temperatures encountered within the clothes dryer. Further, it is preferable that the material forming the flexible packet 2 maintain its flexibility even in a completely dry state. Thus, material such as a fine pored, foamed, flexible polyurethane is preferable for use in forming the flexible packet 2 as compared with a material which becomes hard and brittle when dry, such as a cellulosic sponge material.

The flexible, porous, open-celled sheets used to form the flexible packet may have any desired shape. For example, the sheets may be round, rectangular, triangular or square. Also, the sheets may have a shape which is decorative such as the configuration of a daisy or other flower. In addition, the flexible sheets can be formed from one sheet which is folded over with the fold line constituting one of the seams between the sheets. The expression "a pair of sheets," as used herein, therefore expressly includes the use of a sheet that is folded to form two sheets as well as the use of two sheets which are physically separated and are then joined together to form a packet.

I claim:

1. In combination, a pair of flexible, porous, open-celled sheets joined together in face-to-face relation to form a packet;

said packet including a flexible opening;

said opening having a normally closed position when the sheets forming said packet are in their expanded condition;

said opening being expandable to an open position by squeezing the sides of said packet in a direction along the axis of said opening;

a space defined between said sheets;

said space being enclosed by said sheets except at said opening which leads from the exterior of said packet into said space;

a tablet contained within said space with said space having a configuration that generally conforms with the shape of said tablet;

said tablet formed of a solid fabric softener composition;

said fabric softener composition being partially water soluble, and said sheets having a thickness sufficient to reduce the flow of water through said sheets to a level which prevents complete solution of said tablet from contact with a wet fabric load while permitting partial solution of the tablet and migration of the dissolved fabric softener composition from the interior to the exterior of said packet, whereby the placement of said packet and tablet in a dryer containing a wet fabric load provides migration of the fabric softener composition through the walls of the flexible open-celled sheets by a kneading action with the packet first absorbing water from the load which solubilizes the fabric softener composition on the exterior of the tablet and with the solubilized fabric softener composition then passing through the walls of the open-celled sheets into contact with the fabric load as the packet is compressed by the weight of the fabric load during tumbling of the load within the dryer.

2. The combination of claim 1 wherein said sheets each have a thickness of about one-half inch or more.

3. The combination of claim 1 wherein said sheets are formed of a fine pored, flexible, porous, open-celled polyurethane foam.

4. The combination of claim 3 wherein each of said sheets has a thickness of about one-half to about 1½ inch.

5. The combination of claim 1 wherein said fabric softener composition is a cationic quaternary ammonium salt having an anion with a charge of −1 and a cation with four organic groups bonded to a nitrogen atom with a charge of +1, with said organic groups being either benzyl or an alkyl group containing from 1 to about 20 carbon atoms and at least one of said organic groups being an alkyl group containing from about 12 to about 20 carbon atoms.

6. The combination of claim 5 wherein said fabric softener composition is a dialkyl dimethyl ammonium chloride or an alkyl trimethyl ammonium chloride in which said alkyl contains from about 12 to about 20 carbon atoms and is derived from a long chain fatty acid.

7. The combination of claim 6 wherein said alkyl is a tallow group or a tallow alkoxy group.

8. The combination of claim 1 wherein said sheets have a fine pore structure in which the pore openings range from about one-ninety-sixth to about one-thirty-second of an inch.

9. The combination of claim 3 wherein said sheets have a fine pore structure in which the pore openings range from about one-ninety-sixth to about one-thirty-second of an inch.

10. The combination of claim 4 wherein said sheets have a fine pore structure in which the pore openings range from about one-ninety-sixth to about one-thirty-second of an inch.

* * * * *